US009364088B2

(12) United States Patent
Abene

(10) Patent No.: US 9,364,088 B2
(45) Date of Patent: Jun. 14, 2016

(54) MODULAR SANITATION TRAY SYSTEMS

(76) Inventor: Michael A. Abene, Taunton, MA (US)

(*) Notice: Subject to any disclaimer, the term of this patent is extended or adjusted under 35 U.S.C. 154(b) by 801 days.

(21) Appl. No.: 12/945,425

(22) Filed: Nov. 12, 2010

(65) Prior Publication Data

US 2011/0114585 A1 May 19, 2011

Related U.S. Application Data

(60) Provisional application No. 61/261,320, filed on Nov. 14, 2009.

(51) Int. Cl.
| | |
|---|---|
| *A47B 87/02* | (2006.01) |
| *A61B 19/02* | (2006.01) |
| *B01L 99/00* | (2010.01) |
| *A47B 47/00* | (2006.01) |
| *B01L 9/00* | (2006.01) |

(52) U.S. Cl.
CPC .......... *A47B 87/0253* (2013.01); *A47B 47/0091* (2013.01); *A61B 19/0256* (2013.01); *A61B 19/0271* (2013.01); *B01L 9/00* (2013.01); *B01L 99/00* (2013.01); *A61B 2019/0272* (2013.01); *A61B 2019/0277* (2013.01); *B01L 2200/028* (2013.01); *Y10T 29/49826* (2015.01)

(58) Field of Classification Search
CPC ........... A47B 47/0091; A47B 87/0253; A61B 19/0256; A61B 19/0271; A61B 2019/0272; A61B 2019/0277; B01L 9/00; B01L 99/00; B01L 2200/028
USPC .......... 211/85.13, 126.1, 126.2, 126.3, 126.4, 211/182, 186, 188, 189, 190, 191, 194, 211/85.31, 90.03, 106, 133.2; 108/147.13, 108/147.15, 147.17; 312/140, 205, 228.1, 312/265.1–265.4, 348.3; 52/655.1
See application file for complete search history.

(56) References Cited

U.S. PATENT DOCUMENTS

| | | | | |
|---|---|---|---|---|
| 2,956,705 | A * | 10/1960 | Clingman | 220/683 |
| 3,462,021 | A * | 8/1969 | Hawke et al. | 211/182 |
| 3,834,549 | A * | 9/1974 | Burg et al. | 211/189 |
| 4,129,975 | A * | 12/1978 | Gabriel | 52/655.2 |
| 4,261,470 | A * | 4/1981 | Dolan | 211/191 |
| 4,493,425 | A * | 1/1985 | Yoshida | 211/189 |
| 4,940,149 | A * | 7/1990 | Vineis | 211/186 |
| 5,624,160 | A * | 4/1997 | Koch et al. | 297/452.2 |
| 5,695,081 | A * | 12/1997 | Alkalay | 211/187 |
| 5,715,956 | A * | 2/1998 | Yoshida | 211/182 |
| 5,961,243 | A * | 10/1999 | Michaluk, III | 403/260 |
| 6,004,182 | A * | 12/1999 | Pasin | 446/105 |
| 6,044,990 | A * | 4/2000 | Palmeri | 211/189 |
| 6,099,812 | A | 8/2000 | Allen et al. | |
| 6,164,738 | A | 12/2000 | Dane et al. | |
| 6,314,595 | B1 * | 11/2001 | Price | 5/201 |

(Continued)

*Primary Examiner* — Joshua Rodden
(74) *Attorney, Agent, or Firm* — Banner & Witcoff, Ltd.

(57) ABSTRACT

A sanitation tray system for medical, laboratory, and industrial equipment. This system is modular, stackable, and user customizable. It may be assembled in any number of horizontal or vertical configurations depending on the user's needs and is capable of permitting instruments of varying heights, lengths and widths to be sanitized simultaneously. It is easily assemblable and disassemblable and includes a rack, corners, sides, and dowels. It is lightweight, easy to manufacture, easy to ship, and economical. It is designed to use the least amount of surface area to allow for maximum permeation of sterilants and minimizes the opportunity for pooling of sterilants or retention of particulate matter while decreasing drying time.

19 Claims, 7 Drawing Sheets

(56) References Cited

U.S. PATENT DOCUMENTS

| | | | |
|---|---|---|---|
| 6,460,710 B1* | 10/2002 | Dardashti | 211/184 |
| 6,669,036 B1* | 12/2003 | Yang et al. | 211/181.1 |
| 6,669,213 B2* | 12/2003 | Woerner | 280/47.35 |
| 6,713,029 B1 | 3/2004 | Krafft et al. | |
| 6,827,913 B2 | 12/2004 | Wood | |
| 6,832,580 B2* | 12/2004 | Marchioro | 119/452 |
| 6,874,634 B2 | 4/2005 | Riley | |
| 6,968,962 B2* | 11/2005 | Toma | 211/182 |
| 7,341,148 B2 | 3/2008 | Bettenhausen | |
| 2004/0134869 A1* | 7/2004 | Yang et al. | 211/181.1 |
| 2005/0115913 A1* | 6/2005 | Toma | 211/182 |
| 2007/0104609 A1 | 5/2007 | Powell | |
| 2007/0227994 A1* | 10/2007 | Cho | 211/188 |

\* cited by examiner

FIG. 2B
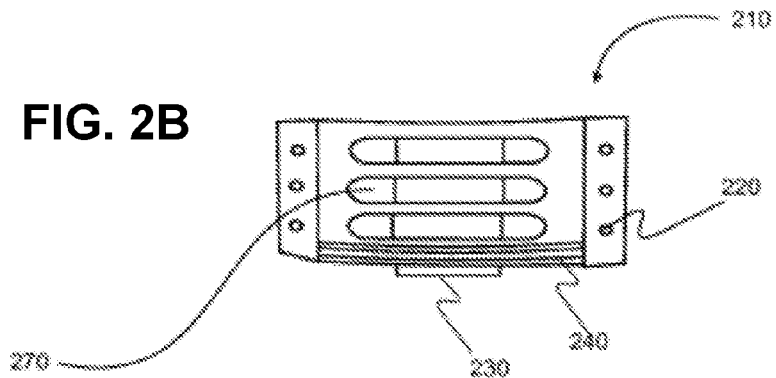
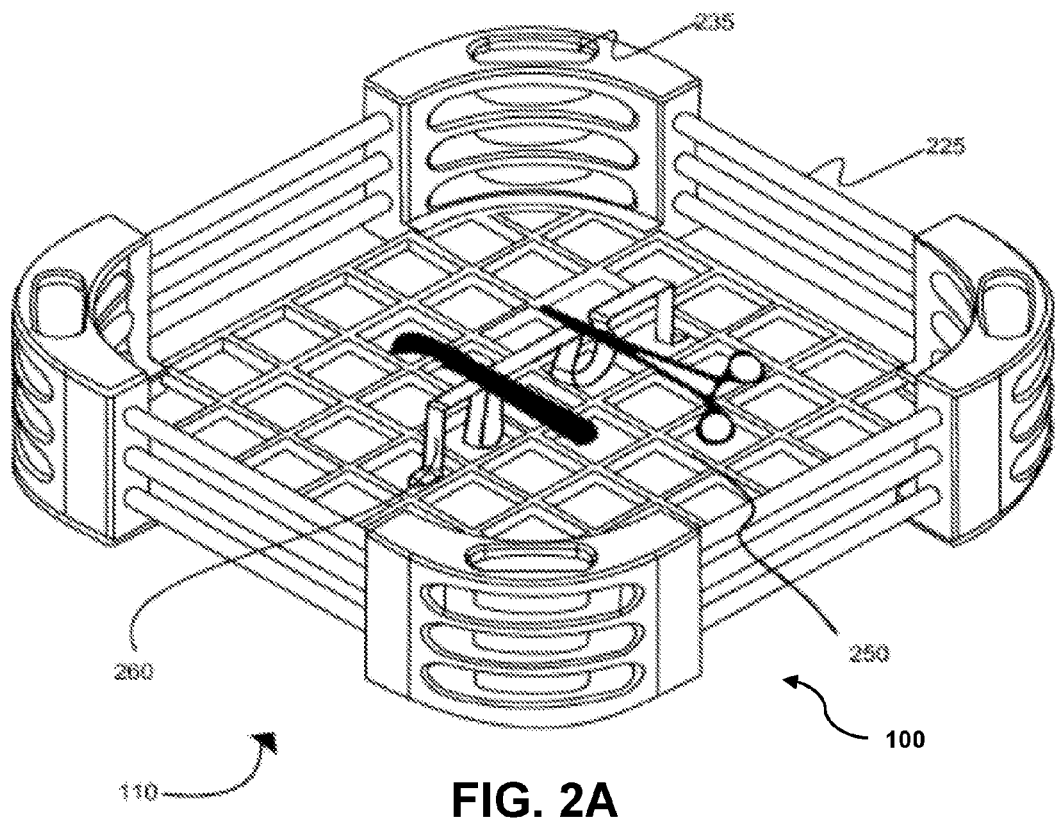
FIG. 2A

US 9,364,088 B2

MODULAR SANITATION TRAY SYSTEMS

This application is a non-provisional of, and claims the benefit of the filing date of U.S. Provisional application No. 61/261,320 filed on Nov. 14, 2009.

BACKGROUND OF THE INVENTION

1. Field of the Invention

The present invention relates generally to the field of sanitation and more specifically relates to sanitation trays.

2. Description of the Related Art

Trays are used to hold laboratory equipment and instruments as they are put through a sanitation/sterilization cycle in a machine such as a dishwasher or an autoclave. These types of trays are commonly used in hospitals, laboratories, and other industrial settings. A typical tray suited for this purpose usually comprises sides and a bottom and occasionally a lid and is generally designed to fit inside a sanitizing machine such as an autoclave or dishwasher. Equipment and instruments used in laboratory or hospital settings such as an operating room are commonly made of a sturdy material such as stainless steel. These tools are designed to be reused once they have gone through a rigorous sanitation process to remove chemical or organic material and pathogens after use. Sanitation machines such as autoclaves or dishwashers are designed to accommodate a variety of tools that are different shapes and sizes and numbers. Typical tools include surgical instruments such as scalpels, hemostats, needles or probes, and glassware such as Ehrlenmeyer flasks, beakers, or cylinders. The above mentioned equipment must be sanitized before and after being used. This is usually accomplished by placing the equipment or instrument in a tray and subjecting the equipment or instrument to a sanitation protocol (such as exposure to extreme temperatures, detergents, or chemicals) for a period of time.

Current sanitization trays are typically one-piece constructions with vent holes that do not have sufficient porosity to permit heat, steam, and other sterilants to permeate the system thoroughly. This also permits sterilants to pool around the instruments within the system, which decreases proper sanitation and increases drying time. Another significant problem with current sanitation tray systems is that particulate matter and blood borne pathogens are not sufficiently removed because there is a significant amount of surface area within the system such that particulate matter (which can include blood borne pathogens or other contaminants and biohazardous material) can pool or get caught in the tray and remain after sanitizing is complete.

Various attempts have been made to provide an effective means for sanitization using a tray. These attempts do not provide adequate means for sterilant flow because they are formed from sheets of material with a number of holes in them. This results in inadequate santization and pooling of sterilants and increases the risk of contamination when the tray is removed from the sanitizing means. These attempts are also not user customizable nor are they readily assemblable or disassemblable, nor can the dimensions be user-specified.

For example, some sanitation trays include a floor fitted into a base and holders to secure instrumentation inside. However, these types of trays have certain disadvantages. They are not modular, stackable with other sizes of trays, nor are they customizable according to user specifications. Further, typical sanitation trays are molded or cut out from a solid piece of material (such as a sheet of metal or block of plastic) whereby portions are carved away until a tray is formed. Sanitation is achieved via these holes. In contrast, the modular sanitation tray is created from empty space using only the minimal amount of material needed to give support to the instruments therein.

Current attempts at stackable trays are similarly flawed. They are not user customizable nor are they modular. Further, these trays are commonly "one size fits all", meaning that the user of a tray is limited to the number and type of instruments he may cleanse in a single cycle of his particular type of sanitation machine. Thus, there is a need for the user to be able to customize his sanitation tray to accommodate his particular set of laboratory equipment. Further, these trays are typically made of a solid piece of metal with holes drilled for aeration. This method of construction similarly has the disadvantage of an increased surface area which increases the opportunity for pooling sterilants and particulate matter retention as well as decreased drying time. None of the current sanitation trays available sufficiently overcomes the problem of an increased surface area nor are they readily assemblable and disassemblable. Further, they cannot be customized to the user's specifications. Ideally, a sanitation tray system should operate reliably as a safe storage means for laboratory and medical equipment as it undergoes the sanitation process. At the same time, a need exists for a durable, customizable, modular system that minimizes the surface area such equipment remains in contact with during the sanitation process.

Thus, what is needed is a sanitation tray system that permits the user to select the size and shape of the system to accommodate his or her individual needs that can be manufactured at a modest expense. There is a need for a sanitation tray that is durable, lightweight, cheap, easy to use, and customizable with surface area to maximize sanitation and minimize drying time. There is also a need for a tray system that permits the user to sanitize many instruments of varying shapes and sizes at the same time without jeopardizing sanitation or sacrificing drying time.

The current invention overcomes these problems in several ways. Ideally, a sanitation tray system should be cheap and easy to manufacture and be customizable to the user's specifications. It should be easily assemblable and disassemblable and incorporate as little surface area as possible to reduce the risks of pooled sterilants and/or left-behind particulate matter. Thus, a need exists for a customizable sanitation tray that can maximize sterilant flow without sacrificing structural integrity and be manufactured at modest expense, easy to ship, and easy to assemble and/or disassemble according to the user's specific needs.

One of the purposes of modular sanitation tray system is to maximize sanitation. One of the ways the system accomplishes this goal is to reduce the amount of surface area in the system. In this manner, the opportunity for residual contaminants and improper cleansing is decreased, while the "total kill" potential of the sanitation machine and the modular sanitation tray system is maximized to allow for complete sanitation. Another purpose of modular sanitation tray system is to provide an easily assemblable tray system that is capable of simultaneously sanitizing groups of laboratory equipment that vary in size, shape, and height.

BRIEF SUMMARY OF THE INVENTION

Accordingly, it is a primary object of the present invention to overcome the aforementioned problems and disadvantages of the related art. Another object of the present invention is to provide a modular, stacking sanitation tray system having enhanced sanitation capabilities and decreased drying time as compared to related art stacking sanitation tray systems, and which provides quick assembly, user customization, decreased shipping costs, and the ability to sanitize instruments of differing sizes at the same time. It should be understood that the present invention is capable of use in equipment that is capable of use in both sanitizing and sterilizing laboratory equipment. The terms can be used interchangeably or to define levels of disinfection. For purposes of clarification, when the term "sanitize" is used to describe the system, it is contemplated within the current invention to provide a tray system that is capable of both "sterilizing" and "sanitizing" laboratory equipment, e.g. removing contaminants and cleaning and/or a "total kill" of all pathogens.

The present invention provides a modular, user-customizable storage, transportation and sanitation tray system for equipment. It provides a safe, effective, convenient, and economical system to accommodate a number of different types of equipment of various shapes and sizes in need of sanitization. A single unit of this system includes a rack, corners, sides, and a plurality of dowels. A single unit of this system may optionally include a plurality of handles, a plurality of holders, and/or a plurality of covers. These units may function as a single unit or a plurality of these units can function in concert to provide a user with any desired configuration of trays to her sanitation needs.

Within a single unit, the corners and sides are attached to each other with the dowels. The dowels may connect a corner piece to another corner piece, a side piece to a corner piece, and/or a side piece to another side piece in a horizontal configuration to permit the user to create a tray system that best serves his or her sanitation needs. A rack may be removably positioned in grooves within the corner or side piece(s). Each corner or side piece may also include a male and/or female coupling element that allows the user to stack the unit on top of another unit. At least one of the surfaces may have any number of holders for securing instruments horizontally or vertically. The holders may be positioned within the system to accommodate the equipment in need of sanitization. A single unit may also attach to another unit to form a system wherein the user specifies the overall shape, height, length, and/or width of the system. In an assembled configuration, equipment within the tray system is stabilized for easy transport into and out of the sanitation machine or in and around the facility at which it is used.

Accordingly, it is an object of this invention to provide a sanitation tray system which is for medical, laboratory, or industrial equipment and which is customized to the individual user's specifications. Still another object of this invention is to provide a sanitation tray system that minimalizes drying time and the potential for pooled sterilants, accumulation of particulate matter and/or blood borne pathogens, and maximizes sanitation of the instrument by using as little solid matter in its construction. A further object of this invention is to provide a method of sanitizing instruments that can be arranged vertically and horizontally. Still another object of this invention is to provide a sanitation tray system that is economical to manufacture, easy and economical to ship, easy to use, modular, stackable, and is readily assemblable and disassemblable. Other features, objects, and advantages of the present invention will become apparent from the following description of a preferred embodiment of the invention taken in conjunction with the accompanying drawings.

BRIEF DESCRIPTION OF THE DRAWINGS

FIG. 2A shows a perspective view of first tray 200 of modular sanitation tray system 100. FIG. 2B shows a plan view of corner receiver 210.

DETAILED DESCRIPTION

Figure 1A:
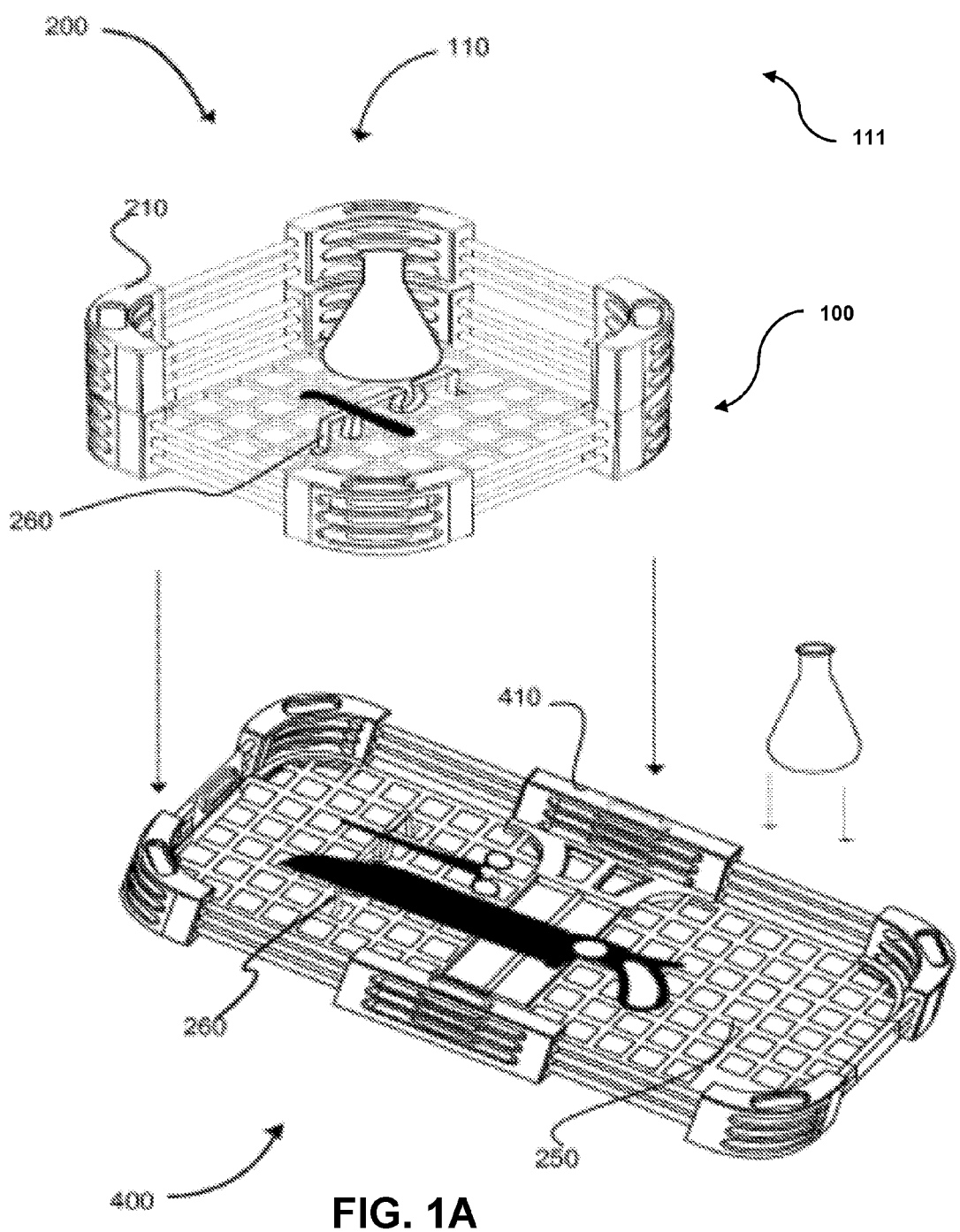
FIG. 1A shows a perspective exploded view of modular sanitation tray system 100 of the present invention, including a corner receiver 210; three first dowel 225 (both illustrated in further detail in FIGS. 2A and 2B); side receiver 410; and second dowel 419 (both illustrated in further detail in FIGS. 4A and 4B). Examples of laboratory equipment frequently sanitized are shown within the tray.

Referring now to FIG. 1A, showing a perspective view of modular sanitation tray system 100 of the present invention. Also shown is an exploded view of a corner receiver 210; three first dowel 225 (both illustrated in further detail in FIGS. 2A and 2B); side receiver 410; and second dowel 419 (both illustrated in further detail in FIGS. 4A and 4B). Examples of laboratory equipment frequently sanitized are shown within the tray. Modular sanitation tray system 100 comprises at least one first tray 200; optionally, at least one second tray 400, and optionally at least one rack 250. Modular sanitation tray system 100 may further comprise an optional instrument holder 260; and an optional handle 405 (shown and discussed in FIGS. 4 and 5). Finally, modular sanitation tray system 100 may optionally comprise a cover or lid (not shown) for added protection and increased sanitation capacity of modular sanitation tray system 100.

Within the present figure, modular sanitation tray system 100 is shown in an in-use condition whereby laboratory equipment is substantially secured within first tray 200 and second tray 400 of modular sanitation tray system 100. Laboratory equipment may comprise surgical instrumentation, glassware, containers, reagents, or any other items in need of sanitation. First tray 200 and second tray 400 are capable of being removably attached to one another via corner receiver 210 and/or side receiver 410. In this manner, the components of modular sanitation tray system 100 are user customizable and function to reduce overall surface area and optimize sanitization within any standard laboratory machine suited for such purpose, such as an autoclave, dishwasher, oven, or other equipment. For exemplary means of an in-use condition, hemostats and a saw are shown in second tray 400, while an Erlenmeyer flask and a scalpel are shown in first tray 200.

It should be understood that the shape and dimensions of modular sanitation tray system 100 are user customizable and that the dimensions are within the acceptable limits as determined by Deutsch Industry Norm ("DIN") standards. Further, each individual component of modular sanitation tray 100 (discussed in detail below) may comprise any material designed to withstand the high temperatures of standard sanitation equipment (such as an autoclave, dishwasher, or oven) including, but not limited to, metals or metal alloys, stainless steel, aluminum, polymers or any other material suitable for such purpose. Within the present embodiment shown, modular sanitation tray system 100 comprises Radel® due to its structural stability, tolerance of high temperatures, ease of manufacture, and cost effectiveness.

As mentioned above, modular sanitation tray system 100 may further comprise a cover or lid for added protection and increased sanitation capacity of modular sanitation tray system 100. The dimensions of the cover are sufficient to cover all or a portion of modular sanitation tray system 100, such as, for example, the cover may cover first tray 200 and/or second tray 400. The cover may be affixed to any portion of modular sanitation tray system 100 via friction fit, clamps, screws, brads, pins, rivets, grommets, adhesives, or any other suitable means necessary to affix the cover to modular sanitation tray 110. The cover may comprise any material designed to withstand the high temperatures of standard sanitation equipment (such as an autoclave, dishwasher, or oven) including, but not limited to, metals or metal alloys, stainless steel, aluminum, polymers or any other material suitable for such purpose.

Referring now to FIG. 2A, first tray 200 of modular sanitation tray system 100 is illustrated. Corner receiver 210 is also shown separately in FIG. 2B. First tray 200 comprises at least one corner receiver 210 and a plurality of first dowel 225. Optionally, first tray 200 may further comprise rack 250 and/or instrument holder 260. By way of example, FIG. 2A illustrates first tray 200 comprising: one (1) rack 250; one (1) instrument holder 260; four (4) corner receiver 210 having with six (6) first aperture 220 each (for a total of twenty-four (24) first aperture 220), and twelve (12) first dowel 225. It should be understood that the dimensions of first tray 200 are user customizable accommodate his or her own laboratory equipment and to fit within his or her own sterilization machine. As a result, the numbers of rack 250, instrument holder 260, corner receiver 210, first aperture 220, and first dowel 225 will vary according to the user's needs. In this manner, first tray 200 is not limited to the dimensions and components as depicted in FIG. 2. It should further be understood that first tray 200 is configured to accommodate several pieces of laboratory equipment of varying shapes, sizes, heights, volumes, and materials. By way of example, FIG. 2A illustrates a scalpel and hemostats secured via instrument holder 260 within first tray 200. First tray 200 may comprise any material designed to withstand the high temperatures of standard sanitation equipment (such as an autoclave, dishwasher, or oven) including, but not limited to, metals or metal alloys, stainless steel, aluminum, polymers or any other material suitable for such purpose. Within the present embodiment shown, the components of first tray 200 comprise Radel® due to its structural stability, tolerance of high temperatures, ease of manufacture, and cost effectiveness.

Corner receiver 210 may comprise first aperture 220; at least one male coupler 230; at least one female coupler 235; a plurality of slot 270; and at least one groove 240. Corner receiver 210 may further comprise a substantially angular configuration that is less than, but not equal to, 180 degrees. By way of example, corner receiver 210 is shown at an approximately 160 degree angle. FIG. 2A further depicts corner receiver 210 with rounded edges. It should be understood that the corner receiver 210 may be convex, concave, pointed, or any other configuration sufficient to house first aperture 220. In this manner, corner receiver 210 works with first aperture 220 and first dowel 225 to enclose rack 250 as shown. Corner receiver 210 may be removably attached to another corner receiver 210 via first dowel 225 which may be placed in first aperture 220 to form the outer confines of first tray 200. In this manner, a substantially quadrangular configuration is created with an inner volume sufficient to house the items to be sanitized.

Corner receiver 210 may further be comprised of a plurality of slot 270. Slot 270 may traverse corner receiver 210 as shown. In this manner, slot 270 further decreases the surface area of corner receiver 210 to decrease the overall surface area of modular sanitation tray system 100. In this manner, slot 270 of corner receiver 210 within first tray 200 of modular sanitation tray system 100 decreases the surface area laboratory instruments remain in contact with during the sanitation process and, as a result, significantly decreases the opportunity for contamination from residual pathogens, and increases the completeness of the sanitation process by maximizing the flow of sterilants.

Figure 3:
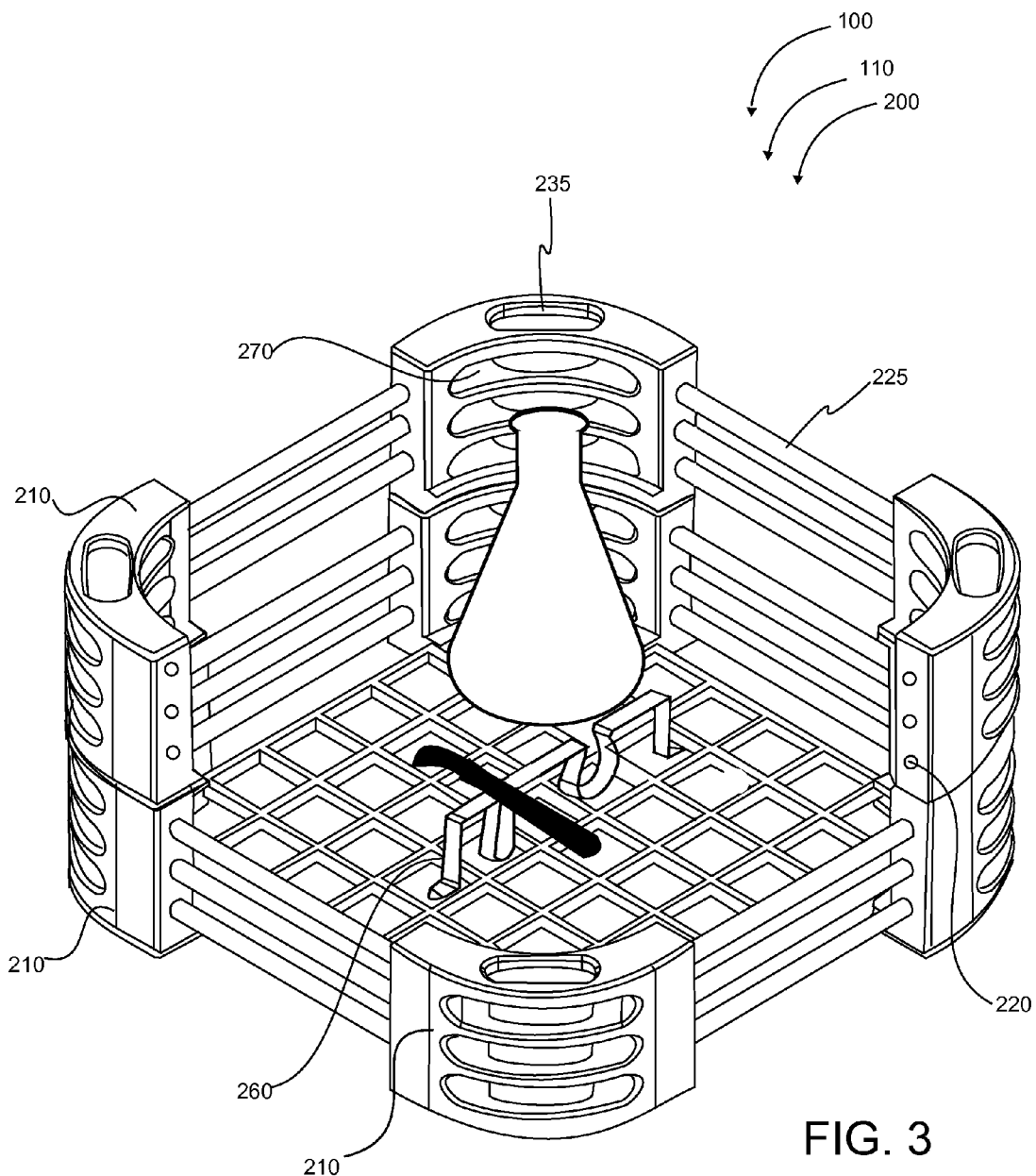
FIG. 3 shows a perspective view of a vertical arrangement of two (2) first tray 200 modular sanitation tray system 100. For exemplary means of an in-use condition, an Erlenmeyer flask, and a scalpel are shown.
Figure 4B:
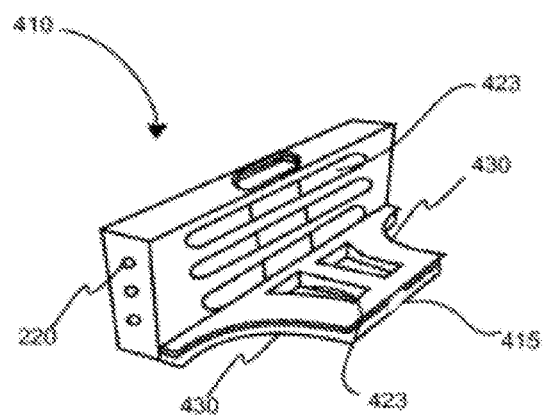
FIG. 4B shows a perspective view of side receiver 410. For exemplary means of an in-use condition, hemostats and a saw are shown.
Figure 4A:
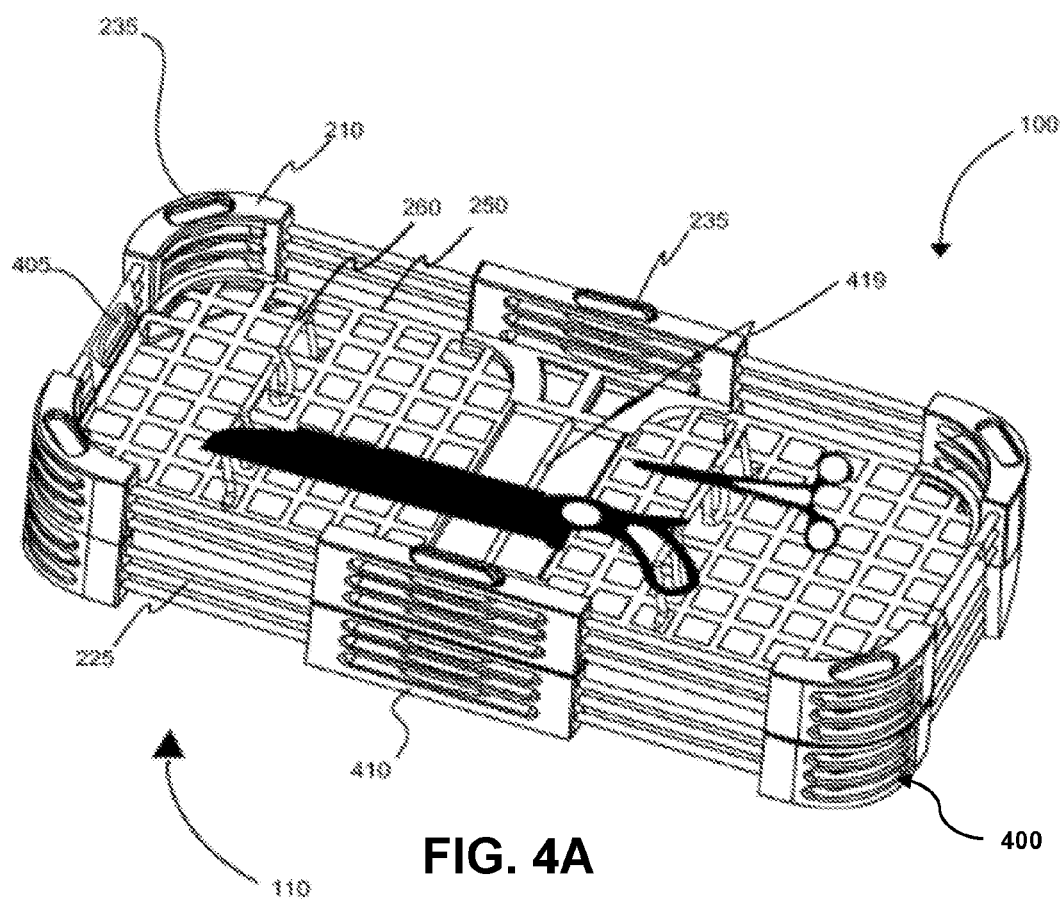
FIG. 4A illustrates a perspective view of second tray 400 of modular sanitation tray system 100.
Figure 5:
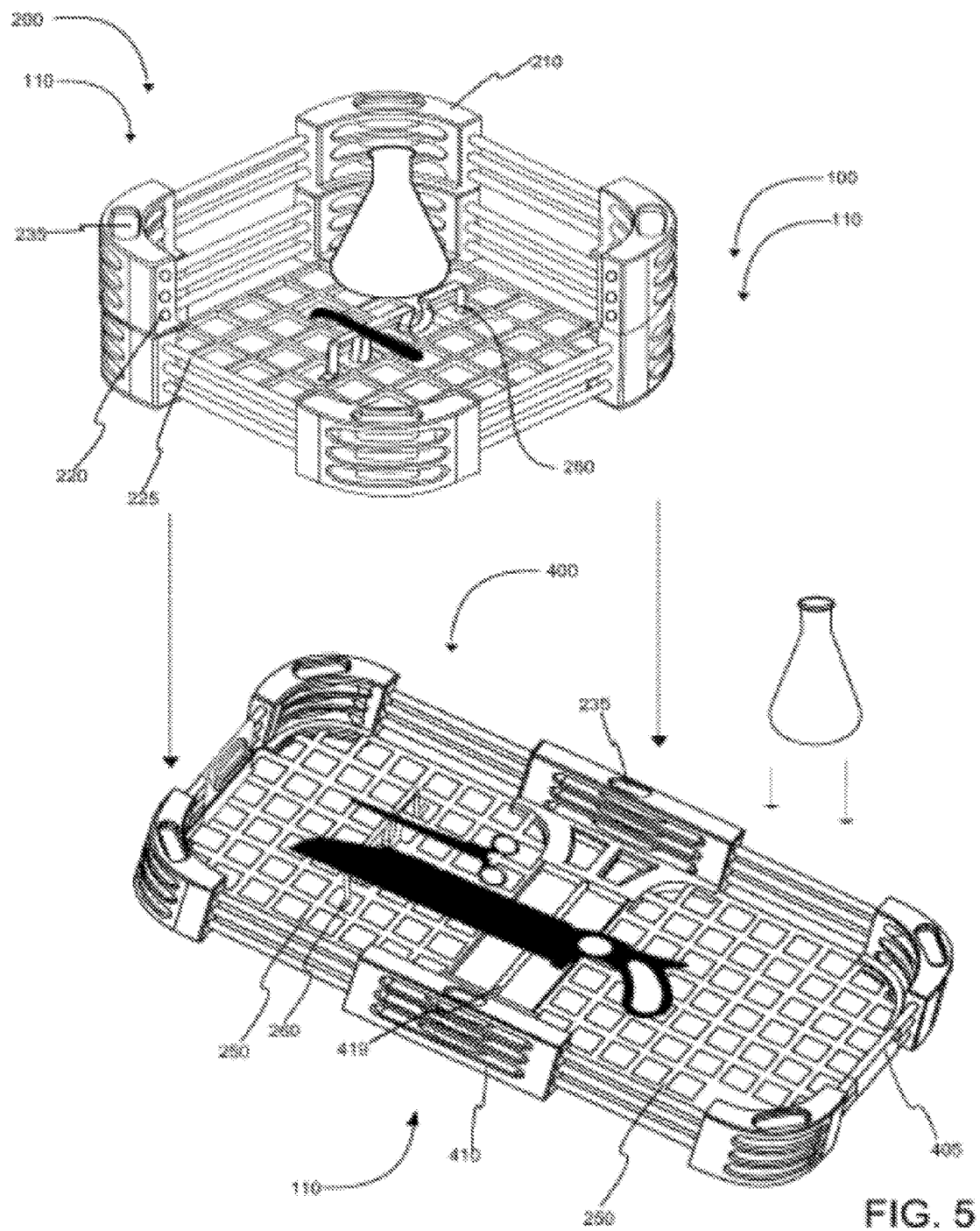
FIG. 5 illustrates the kit of the tray system of FIG. 1 in an in-use condition.

Corner receiver 210 may further comprise at least one male coupler 230 and/or at least one female coupler 235 to allow vertical stacking of at first tray 200 and/or second tray 400 (discussed in further detail in FIGS. 3, 4A and 5). Male coupler 230 may be an appendage of corner receiver 210 and/or side receiver 410. Further, male coupler 230 may be any type of outgrowth sufficient to create a secure hold with female coupler 235. Male coupler 230 may further serve the purpose of elevating modular tray system 100 from the substrate of the sanitation machine, thereby maximizing the surface area sterilants are able to permeate modular sanitation tray system 100. FIG. 2A depicts male coupler 230 substantially on the underside of corner receiver 210 as shown. In an alternative embodiment, male coupler 230 may be placed on or near the top or on the sides of corner receiver 210 (not shown).

Female coupler 235 may comprise a depression, divot, concavity, or any other indentation sufficient to removably receive male coupler 230. The dimensions of female coupler 235 are directly proportional to and/or complementary to the dimensions of male coupler 230 such that first tray 200 is capable of being removable attached to second tray 400 using male coupler 230 and/or female coupler 235 as a securing means. Further, female coupler 235 further decreases the surface area of corner receiver 210 to decrease the overall surface area of modular sanitation tray system 100. In this manner, first tray 200 of modular sanitation tray system 100 maximizes sanitation of laboratory equipment and significantly decreases the opportunity for contamination from residual pathogens while increasing completeness of the sanitation process by maximizing the flow of sterilants.

Corner receiver 210 may further comprise at least on first aperture 220 and at least one first dowel 225. Preferably, corner receiver 210 has a plurality of first aperture 220 to provide suitable frictional securing means for first dowel 225. First aperture 220 may comprise a substantially cylindrical inner volume sufficient to removably receive first dowel 225. Finally, first aperture 220 may be located on the proximal or distal portion of corner receiver 210. First dowel 225 may comprise a rod within the particular embodiment shown. In this manner, first dowel 225 fits into first aperture 220 in a manner that creates an angle sufficient to create a poly-sided configuration of modular sanitation tray system 100 (discussed in detail in FIG. 5). FIG. 2A depicts first dowel 225 and first aperture 220 in a substantially cylindrical configuration, however, it should be understood that the shape of first dowel 225 and first aperture 220 may be of any shape sufficient to provide a border to first tray 200, such as, for example, a rectangular or triangular bar. It is contemplated within the current invention that varying shapes may be created by varying the number of dowels and receivers.

As mentioned above, first dowel 225 may comprise a circumferential outer volume that is substantially proportional to the volume of first aperture 220 to permit first dowel 225 to form a friction fit within the inner volume of first aperture 220 of corner receiver 210. In this configuration, first dowel 225 and corner receiver 210 operate to create a secure enclosure using the least amount of surface area possible while still maintaining structural integrity. Corner receiver 210 may be removably attached to another corner receiver 210 via first dowel 225 which may be placed in first aperture 220 to form the outer confines of modular sanitation tray 110 as shown, resulting in a substantially quadrangular configuration of first tray 200. In this manner, first tray 200 functions to house the items to be sanitized. It should be understood that corner receiver 210, first aperture 220, and first dowel 225 may work in concert to create the outer perimeter of first tray 200. By way of example, first tray 200 is shown in a substantially square shape. Finally, first dowel 225 further accomplishes the goal of reducing the overall surface area of first tray 200 while still maintaining its structural stability. In this manner, first dowel 225 functions as an integral unit of first tray 200 within modular sanitation tray system 100 to decrease drying time and minimize retention of contaminants once the sanitation process is complete. As a result, the opportunity for improper sanitation and residual contaminants is significantly decreased.

Corner receiver 210 may further comprise at least one groove 240 for removably receiving a plurality of rack 250. Groove 240 may positioned substantially near the bottom of corner receiver 210 as shown. The dimensions of groove 240 are proportional to rack 250 so as to permit it first rack 250 to form a friction fit groove 240 of corner receiver 210 as shown. Rack 250 fits into groove 240 in a similar manner as that of a dado joint. In other embodiments, rack 250 may be attached to corner receiver 210 in any manner sufficient to accomplish a secured hold such as clamps, brads, snaps, pegs, hooks, ties, or other suitable attaching means. Further, it should be understood that other joints such as tongue and groove, dovetail, box, finger, or any other suitable type of fastening means may be used to accomplish a secure assembly of groove 240 and rack 250. In other embodiments, groove 240 may be located in any portion of corner receiver 210 to function as a receiving means for rack 250, such as, for example, the top or middle of corner receiver 210 Groove 240 further serves to decrease the overall weight of modular sanitation tray system 100 and increases the frictional surface area for maximum retention of rack 250.

Optionally, first tray 200 may further comprise rack 250. Rack 250 as shown comprises a substantially grid-like arrangement. It should be understood that rack 250 may be any framework capable of supporting instrument holder 260 and/or laboratory equipment within first tray 200. In this manner, rack 250 accomplishes the goal of providing a substrate for instrument holder 260 for securing laboratory equipment in need of sanitizing within modular sanitation tray system 100. Rack 250 further accomplishes the goal of reduced surface area to minimize retention of contaminants once the sanitation process is complete and to reduce the overall weight, cost of manufacture, and shipping costs of modular sanitation tray system 100. Finally, rack 250 may comprise any material designed to withstand the high temperatures of standard sanitation equipment (such as an autoclave, dishwasher, or oven) including, but not limited to, metals or metal alloys, stainless steel, aluminum, polymers or any other material suitable for such purpose. Within the present embodiment shown, modular sanitation tray system 100 comprises Radel® due to its structural stability, tolerance of high temperatures, ease of manufacture, and cost effectiveness.

Optionally, modular sanitation tray system 100 may further comprise at least one instrument holder 260 for horizontally and/or vertically holding at least one piece of laboratory equipment within modular sanitation tray system 100. In alternative embodiments, instrument holder 260 may be affixed to first dowel 225 (not shown). Instrument holder 260 may comprise biasing means as shown. In alternative embodiments instrument holder 260 may further comprise latching means, clamping means, or other such suitable methods of securing an item within modular sanitation tray system 100.

As mentioned above, instrument holder 260 of modular sanitation tray system 100 may be used to vertically and/or horizontally secure laboratory equipment within modular sanitation tray system 100. By way of example, FIG. 2 depicts instrument holder 260 securing hemostats and a scalpel in a horizontal position within first tray 200. Items to be sanitized are placed on or in instrument holder 260 which may be attached to rack 250, corner receiver 210, side receiver 410 or any other suitable portion of modular sanitation tray 100 to accomplish the task of securing items within the system as they undergo sanitization. In alternative embodiments, instrument holder 260 may be a spring fit, clasp, adhesives, or any other suitable configuration to accomplish the task of securing items within modular sanitation tray 110. Further, instrument holder 260 may be attached to any portion of second tray 400 via clamps, screws, brads, pins, rivets, grommets, adhesives, or any other suitable means necessary to affix instrument holder 260 first tray 200. Finally, instrument holder 260 may comprise any material designed to withstand the high temperatures of standard sanitation equipment (such as an autoclave, dishwasher, or oven) including, but not limited to, metals or metal alloys, stainless steel, aluminum, polymers or any other material suitable for such purpose.

Referring now to FIG. 3, showing a perspective view of a vertical arrangement of two (2) first tray 200 of modular sanitation tray system 100. As discussed above, corner receiver 210 may comprise male coupler 230 and female coupler 235. Within this optional embodiment, first tray 200 may be removably attached to another first tray 200 on the vertical axis via male coupler 230 and female coupler 235. In this manner, a plurality of corner receiver 210 may be vertically stacked whereby male coupler 230 engages female coupler 235 as shown. In this manner, the user is capable of vertically arranging a plurality of first tray 200. It should be noted that within alternate embodiments, first assembled tray may include a plurality of rack 250, and/or a plurality of instrument holder 260. It should be further understood that rack 250 is optional, and the user may wish to exclude rack 250 from first tray 200. In this manner, first tray 200 may comprise a single taller vertical unit. In the alternative, the user may include rack 250, for example, per four (4) corner receiver 210. First tray 200 as depicted in FIG. 3 comprises of one (1) rack 250; seven (7) corner receiver 210; eighteen (18) first dowel 225; and one instrument holder 260. It should be understood that the user is capable of stacking any number of first tray 200 to accommodate his or her unique laboratory equipment and/or sanitation machines.

This embodiment permits the user to customize a vertical configuration to suit his or her sanitation needs depending on the type and/or size and/or height of item to be sanitized and within the confines of his or her particular sanitation device. This embodiment permits the user to sanitize items of differing heights (such as, for example, an Erlenmeyer flask and a scalpel) at the same time and maximize the internal cavity of his or her particular sanitation device without compromising complete sanitation and reducing the risk of pooled reagents or particulate matter after sanitation is complete. By way of example, FIG. 3 demonstrates two (2) vertically assembled of first tray 200. It should be understood that modular tray system is not limited to a particular number of first tray 200 or a particular number of second tray: the dimensions or modular tray systems 100 are determined by user preference to accommodate the user's particular equipment and sterilization/sanitation equipment. As mentioned above, a plurality of first tray 200 may be stacked with or without rack 250. In this manner, first tray 200 is capable of receiving laboratory equipment of varying sizes and heights in need of sanitizing.

Referring now to FIG. 4A, a perspective view of second tray 400 of modular sanitation tray system 100 is illustrated. Side receiver 410 is also shown separately in FIG. 4B. Second tray 400 comprises at least one corner receiver 210, at least one side receiver 410, at least one second aperture 415, at least one second dowel 419, a plurality of first dowel 225 and a plurality of first aperture 220. Optionally, second tray 400 may further comprise rack 250, a cover (not shown) and/or instrument holder 260. By way of example, FIG. 4A illustrates second tray 400 comprising: two (2) rack 250; (2) instrument holder 260; eight (8) corner receiver 210 having six (6) first aperture 220 each (for a total of forty-eight (48) first aperture 220). FIG. 4 further illustrates second tray 400 having four (4) side receiver 410 having six (6) first aperture 220 each for a total of twenty-four (24) aperture 220; one (1) second aperture 415; and one (1) second dowel 419. Finally, FIG. 4A depicts second tray 400 comprising thirty-six (36) first dowel 225. It should be understood that the dimensions of second tray 400 are user customizable accommodate his or her own laboratory equipment and to fit within his or her own sterilization machine. As a result, the numbers of corner receiver 210; side receiver 410; rack 250, instrument holder 260, corner receiver 210, first dowel 225 and second dowel 419 will vary according to the user's needs. In this manner, second tray 400 is not limited to the dimensions and components as depicted in FIG. 4A-B. It should further be understood that second tray 400 is configured to accommodate several pieces of laboratory equipment of varying shapes, sizes, heights, volumes, and materials. As a result, second tray 400 may be arranged to form any conceivable poly sided multi linear configuration of reasonable portions.

For exemplary means of an in-use condition, FIG. 4A illustrates a saw and hemostats secured via instrument holder 260 within second tray 400. Second tray 400 may comprise any material designed to withstand the high temperatures of standard sanitation equipment (such as an autoclave, dishwasher, or oven) including, but not limited to, metals or metal alloys, stainless steel, aluminum, polymers or any other material suitable for such purpose. Within the present embodiment shown, the components of second tray 400 comprise Radel® due to its structural stability, tolerance of high temperatures, ease of manufacture, and cost effectiveness.

Side receiver 410 may comprise at least one second aperture 415, at least one first aperture 220, a plurality of side receiver slot 423, and at least one side receiver groove 430. Side receiver 410 may comprise a substantially "L" shaped configuration with the topmost portion comprising a substantially linear configuration of approximately 180 degrees. In this manner, side receiver 410 may be removably attached to corner receiver 210 with first aperture 220 and first dowel 225 to enclose a plurality of rack 250 as shown. In alternative embodiments, side receiver 410 may removably attached to another side receiver 410 via first aperture 220 and first dowel 225 (not shown). Side receiver 410 may be removably attached to corner receiver 210 and/or side receiver 410 via first dowel 225 which may be placed in first aperture 220 to form the outer confines of second tray 400 of modular sanitation tray 100. In this manner, a substantially quadrangular configuration is created with an inner volume to house the user specified items to be sanitized.

Side receiver 410 may further be comprised of a plurality of side receiver slot 423. Side receiver slot 423 may traverse side receiver 410 on the vertical plane and/or on the horizontal plane as shown. Side receiver slot 423 may further decrease the surface area of side receiver 410 to decrease the overall surface area of modular sanitation tray system 100. In this manner, side receiver slot 423 of side receiver 410 within second tray 400 of modular sanitation tray system 100 maximizes sanitation of laboratory equipment and significantly decreases the opportunity for contamination from residual pathogens while increasing completeness of the sanitation process by maximizing the flow of sterilants.

Side receiver 410 may further comprise at least one male coupler 230 and/or at least one female coupler 235 to allow vertical stacking of at first tray 200 and/or second tray 400. The dimensions of male coupler 230 and female coupler 235 permit the user to stack corner receiver 210 and side receiver 410 interchangeably. By way of example, FIG. 4A depicts two (2) second tray 400 forming the base of modular sanitation tray system 100 with one (1) second tray 400 to form the top portion of modular sanitation tray system 100 via male coupler 230 and female coupler 235. Male coupler 230 (shown in FIG. 2A) may be an appendage of side receiver 410. Further, male coupler 230 may be any type of outgrowth sufficient to create a secure hold with female coupler 235. Male coupler 230 may further serve the purpose of elevating modular tray system 100 from the substrate of the sanitation machine, thereby maximizing the surface area sterilants are able to permeate modular sanitation tray system 100. In an alternative embodiment, male coupler 230 may be placed on or near the top or bottom of side receiver 410 (not shown).

Female coupler 235 may comprise a depression, divot, concavity, or any other indentation sufficient to removably receive male coupler 230. The dimensions of female coupler 235 are directly proportional and/or complementary to the dimensions of male coupler 230 such that first tray 200 is capable of being removable attached to second tray 400 using male coupler 230 and/or female coupler 235 as a securing means. Further, female coupler 235 further decreases the surface area of corner receiver 210 and as a result, the overall surface area of modular sanitation tray system 100. In this manner, second tray 400 of modular sanitation tray system 100 maximizes the flow of sterilants to optimize sanitation of laboratory equipment and significantly decreases the opportunity for contamination from residual pathogens.

Side receiver 410 may further comprise at least on first aperture 220 and at least one first dowel 225. Preferably, side receiver 410 has a plurality of first aperture 220 to provide suitable frictional securing means for first dowel 225. First aperture 220 may comprises a substantially cylindrical inner volume sufficient to removably receive first dowel 225. Finally, first aperture 220 may be located on the proximal or distal portion of corner receiver 210. First dowel 225 may comprise a rod within the particular embodiment shown. In this manner, first dowel 225 fits into aperture in a manner that creates an angle sufficient to create a poly-sided configuration of modular sanitation tray system 100. FIG. 5 depicts first dowel 225 and first aperture 220 in a substantially cylindrical configuration, however, it should be understood that the shape of first dowel 225 and first aperture 220 may be of any shape sufficient to provide a border to second tray 400, such as, for example, a rectangular or triangular bar.

As mentioned above, first dowel 225 may comprise a circumferential outer volume that is substantially proportional to inner volume to permit first dowel 225 to form a friction fit within the inner volume of first aperture 220 of corner receiver 210. In this configuration, first dowel 225 and corner receiver 210 operate to create an outer border of second tray 400 by using the least amount of surface area possible while still maintaining structural integrity. Side receiver 410 may be removably attached to a corner receiver 210 via first dowel 225 which may be placed in first aperture 220 of side receiver 410 to form the outer confines of modular sanitation tray 100 as shown resulting in a substantially quadrangular configuration of first tray 200 is formed. In alternative embodiments (not shown) side receiver 410 may attach to a second side receiver 410 via first dowel 225 and first aperture 220. In this manner, second tray 400 functions to house the items to be sanitized. It should be understood that corner receiver 210, first aperture 220, and first dowel 225 may work in concert to create the outer perimeter of second tray 400. By way of example, second tray 400 is shown in a substantially rectangular shape.

First dowel 225 further accomplishes the goal of reducing the overall surface area of first tray 200 while still maintaining its structural stability. In this manner, first dowel 225 functions as an integral unit of second tray 400 within modular sanitation tray system 100 to decrease drying time and minimize retention of contaminants once the sanitation process is complete. As a result, the opportunity for improper sanitation and residual contaminants is significantly decreased. Finally, side receiver 410 may comprise any material designed to withstand the high temperatures of standard sanitation equipment (such as an autoclave, dishwasher, or oven) including, but not limited to, metals or metal alloys, stainless steel, aluminum, polymers or any other material suitable for such purpose. Within the present embodiment shown, modular sanitation tray system 100 comprises Radel® due to its structural stability, tolerance of high temperatures, ease of manufacture, and cost effectiveness.

Side receiver 410 may further comprise at least one second aperture 415 and at least one second dowel 419. Second aperture 415 may comprise a substantially cylindrical inner volume sufficient to removably receive second dowel 419. FIG. 5 depicts second aperture 415 placed within the lower plane of side receiver 410, and substantially within side receiver groove 430. It should be understood that second aperture 415 may be located on the proximal or distal portion of side receiver 410 and may be located in the upper or lower portion of side receiver 410. Further, second aperture 415 may be arranged in a substantially parallel relationship with rack 250. Second aperture 415 may comprise an inner volume sufficient to removably receive at least one second dowel 419.

Second dowel 419 as shown may be substantially cylindrical and may comprise a circumferential outer volume that is substantially proportional to the inner volume of second aperture 415 to permit second dowel 419 to accomplish a friction fit within the inner volume of second aperture 415 of side receiver 410. Second dowel 419 may comprise a rod within the particular embodiment shown. In this manner, second dowel 419 fits into second aperture 415 in a manner that functions to connect two side receiver 410 as shown. In this manner, second dowel 419 accomplishes the goal of increased structural integrity of second tray 400 FIG. 5 depicts second dowel 419 and second aperture 415 in a substantially cylindrical configuration, however, it should be understood that the shape of second dowel 419 and second aperture 415 may be of any shape sufficient to provide a border to second tray 400, such as, for example, a rectangular or triangular bar.

As mentioned above, Second dowel 419 may comprise a circumferential outer volume that is substantially proportional to inner volume to permit Second dowel 419 to form a friction fit within the inner volume of Second aperture 415 of side receiver 410. In this configuration, dowel and corner receiver 210 operate to create a secure environment using the least amount of surface area possible while still maintaining structural integrity. Second dowel 419 further accomplishes the goal of reducing the overall surface area of second tray 400 while still maintaining its structural stability. In this manner, second dowel 419 functions as an integral unit of second tray 400 within modular sanitation tray system 100 to decrease drying time and minimize retention of contaminants once the sanitation process is complete. As a result, the opportunity for improper sanitation and residual contaminants is significantly decreased.

Side receiver 410 may further comprise at least one side receiver groove 430 for removably receiving a plurality of rack 250. Side receiver groove 430 as depicted in FIG. 5 is located on the horizontal plane of side receiver 410. It should be understood that side receiver groove 430 may be located on any portion of side receiver 410 in any manner to permit it to removably receive rack 250, such as the top most portion, the middle portion or the back. Further, side receiver groove 430 may comprise two substantially convex corners with a substantially planar midsection. In this manner, Side receiver groove 430 accomplishes the goal of connecting a plurality of rack 250 as shown. It should be understood that Side receiver groove 430 may be any shape sufficient to accommodate at least two (2) rack 250. Side receiver groove 430 may be configured to receive at least 2 of corner of rack 250 as shown. In this manner, Side receiver groove 430 functions to permit the user to design a configuration of modular sanitation tray 100 containing a specified number of rack 250, side receiver 410, and corner receiver 210.

Side receiver groove 430 may be positioned substantially near the bottom of corner receiver 210 as shown. The dimensions of side receiver groove 430 are proportional to rack 250 so as to permit it first rack 250 to form a friction fit with groove 240 of corner receiver 210. Rack 250 fits into side receiver groove 430 in a similar manner as that of a dado joint as shown. In other embodiments, rack 250 and side receiver groove 430 may be assembled in any manner sufficient to accomplish a secured hold such as clamps, brads, snaps, pegs, hooks, ties, or other suitable attaching means. Further, it should be understood that other joints such as tongue and groove, dovetail, box, finger, or any other suitable type of fastening means may be used to accomplish a secure assembly of groove 240 and rack 250. In other embodiments, side receiver groove 430 may be located in any portion of side receiver 410 to function as a receiving means for rack 250, such as, for example, the top or middle of corner receiver 210. Side receiver groove 430 further serves to decrease the overall weight of modular sanitation tray system 100 and increases the frictional surface area for maximum retention of rack 250.

Optionally, Second tray 400 may further comprise rack 250. Rack 250 may be received by side receiver groove 430 via side receiver 410. Rack 250 as shown comprises a substantially grid-like arrangement. It should be understood that rack 250 may be any framework capable of supporting instrument holder 260 and/or laboratory equipment within first tray 200. In this manner, rack 250 accomplishes the goal of providing a substrate for instrument holder 260 for securing laboratory equipment in need of sanitizing within modular sanitation tray system 100. In alternative embodiments, the user may omit rack 250 to create a configuration to accommodate taller equipment in need of sanitizing, such as a graduated cylinder or a surgical tray. Rack 250 further accomplishes the goal of reduced surface area to minimize retention of contaminants once the sanitation process is complete and to reduce the overall weight, cost of manufacture, and shipping costs of modular sanitation tray system 100. Finally, rack 250 may comprise any material designed to withstand the high temperatures of standard sanitation equipment (such as an autoclave, dishwasher, or oven) including, but not limited to, metals or metal alloys, stainless steel, aluminum, polymers or any other material suitable for such purpose. Within the present embodiment shown, rack 250 comprises Radel® due to its structural stability, tolerance of high temperatures, ease of manufacture, and cost effectiveness.

Optionally, modular sanitation tray system 100 may further comprise at least one instrument holder 260 for horizontally and/or vertically holding at least one piece of laboratory equipment within modular sanitation tray system 100. In alternative embodiments, instrument holder 260 may be affixed to first dowel 225 (not shown). Instrument holder 260 may comprise biasing means as shown. In alternative embodiments instrument holder 260 may further comprise, latching means, clamping means, or other such suitable methods of securing an item within modular sanitation tray system 100.

As mentioned above, instrument holder 260 of modular sanitation tray system 100 may be used to vertically and/or horizontally secure laboratory equipment within modular sanitation tray 110. By way of example, FIG. 5 depicts instrument holder 260 securing hemostats and a saw in a horizontal position within second tray 400. Items to be sanitized may be placed on or in instrument holder 260 which may be attached to rack 250, corner receiver 210, side receiver 410, or any other suitable portion of modular sanitation tray 100 to accomplish the task of securing items within the system as they undergo sanitization. In alternative embodiments, instrument holder 260 may be a spring fit, clasp, adhesives, or any other suitable configuration to accomplish the task of securing items within modular sanitation tray 210. Further, instrument holder 260 may be attached to second tray 400 via clamps, screws, brads, pins, rivets, grommets, adhesives, or any other suitable means necessary to affix instrument holder 260 to modular sanitation tray 110. Finally, instrument holder 260 may comprise any material designed to withstand the high temperatures of standard sanitation equipment (such as an autoclave, dishwasher, or oven) including, but not limited to, metals or metal alloys, stainless steel, aluminum, polymers or any other material suitable for such purpose.

As mentioned previously, modular sanitation tray system 100 may further comprise handle 405. Handle 405 may be affixed to first dowel 225 of second tray 400 as shown. Further, handle 405 may be affixed to corner receiver 210, side receiver 410, or any component of first tray 200 and/or second tray 400 to accomplish a means by which the user may grasp, suspend, and/or carry modular sanitation tray system 100. In this manner, handle 405 permits the user to grip and transport modular sanitation tray system 100 into or out of sanitation device and to other areas where sanitized items are used such as an operating room or laboratory. Handle 405 may be affixed to second tray 400 or first tray 200 (not shown) via clamps, screws, brads, pins, rivets, grommets, adhesives, or any other suitable means necessary to affix the at least one handle 405 to modular sanitation tray 110. Finally, handle 405 may comprise any material designed to withstand the high temperatures of standard sanitation equipment (such as an autoclave, dishwasher, or oven) including, but not limited to, metals or metal alloys, stainless steel, aluminum, polymers or any other material suitable for such purpose.

Figure 1B:
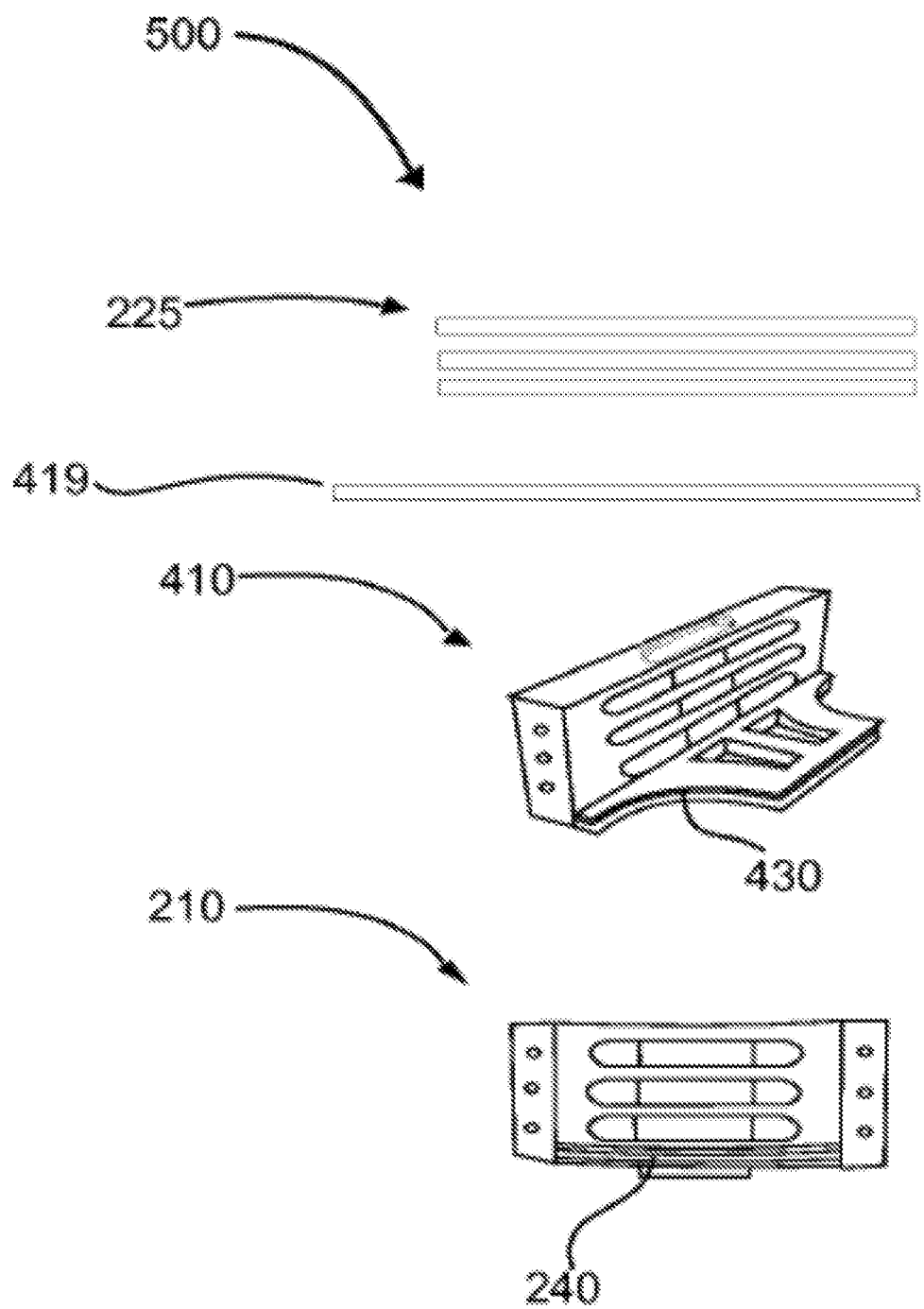
FIG. 1B shows a schematic view of a kit 500 including components of a modular sanitation tray system 100 of the present invention.

Referring now to FIGS. 1B and 5, illustrating kit 500 of modular tray system 100 shown in FIGS. 1A-4B. Kit 500 may include at least one first tray 200; at least one second tray 400; at least one cover (not shown); and at least one handle 405. Corner receiver 210 may be removably attached to another corner receiver 210 via first dowel 225 which may be placed in first aperture 220 of side receiver 410. In alternative embodiments, corner receiver 210 may be removably attached to another corner receiver 210 via first dowel 225 which may be placed in first aperture 220 of corner receiver 210. In other embodiments, side receiver 410 may be removably attached to another side receiver 410 via first dowel 225 which may be placed in first aperture 220 of side receiver 410. Further, modular sanitation tray system 100 may comprise only first tray 200 and/or only second tray 400 and/or a combination of first tray 200 and second tray 400. In this way the present invention is customizable and may be assembled according to user-preference based on the application desired and available space in the sanitizing mechanism. As discussed previously, kit 500 may comprise vertical and horizontal configurations. Kit 500 contents may comprise the various components made from different materials as mentioned above. Examples of equipment to be sanitized within modular tray system 100 as shown in FIG. 5 include hemostats, a saw, a scalpel, and two (2) Erlenmeyer flasks.

By way of example, FIG. 5 shows two (2) first tray 200 and one (1) second tray 400 removably attached to each on the vertical and/or horizontal axis via the male coupling element 230 and/or the female coupling element 240. This option allows the user to further customize modular tray system 100 according to his or her particular sanitation device and depending on the items the user wishes to sanitize individually or in groups. Optionally, a plurality of side receiver 410 may be used to increase the size and shape of modular sanitation tray system 100 thus creating a substantially multiplanar configuration (e.g. the resultant shape may be any shape wherein the sides are parallel or perpendicular in relation to each other to form a vertical or horizontal square, rectangle, "L" shape, "I" shape, "T" shape, or any other user preferred rectilinear configuration. As depicted in FIG. 5 modular sanitation tray system 100 comprises one (1) handle 405, one (1) second tray 400 comprising two (2) rack 250; two side receiver 410; four (4) corner receiver 210, eighteen (18) first dowel 225, one (1) second dowel 419, one (1) instrument holder 260; and two (2) first tray 200 comprising one (1) rack 250, seven (7) corner receiver 210, twelve (12) first dowel 225 and one (1) instrument holder 260. By way of example, a hemostat and a saw are shown in second tray 400, while an Erlenmeyer flask and a scalpel are shown in first tray 200.

Figure 6:
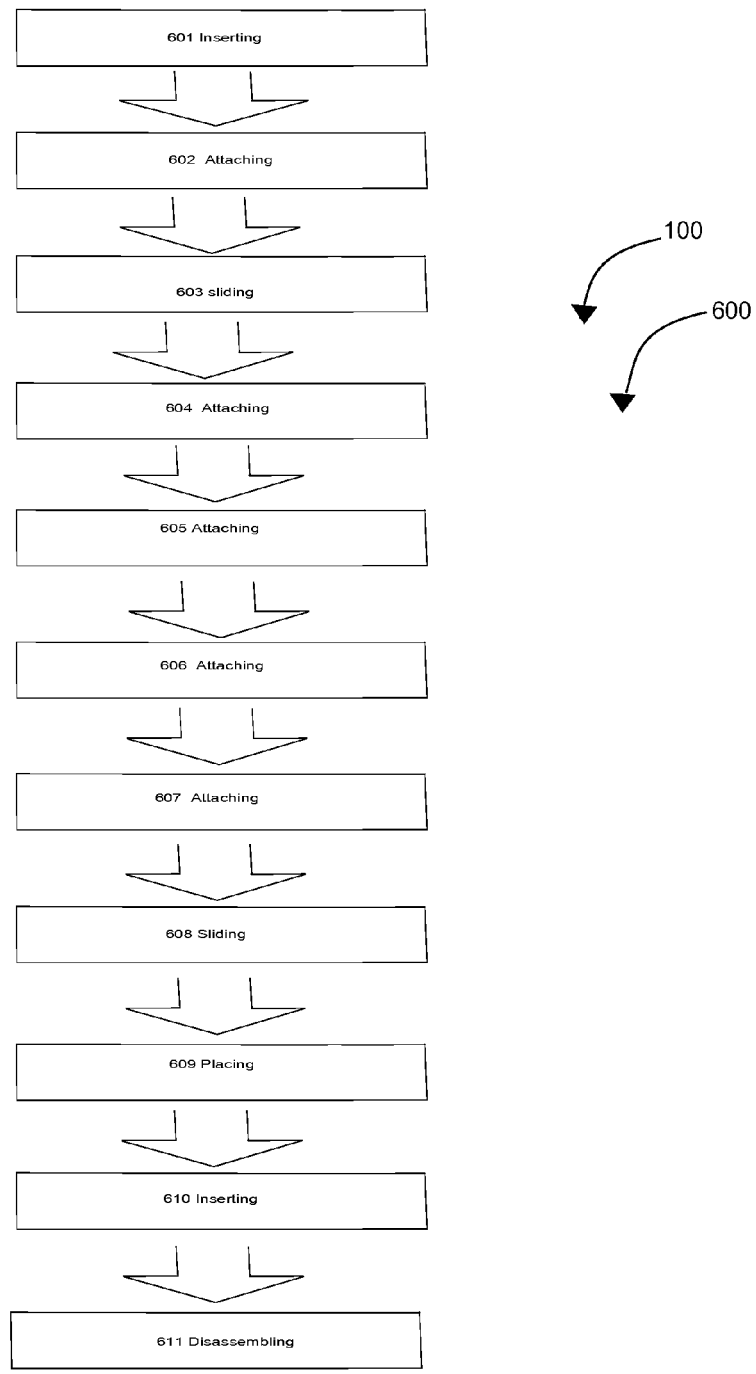
FIG. 6 shows a method of use of the sanitation tray system of FIGS. 1 through 5.

Referring now to FIG. 6, modular sanitation tray system 100 provides a system whereby the components may be manufactured separately providing for decreased costs related to shipping. Further, the user has the additional benefit that the system is easily assemblable and disassemblable for transport between locations and in/or out of the sanitation machine. The user also benefits in that they may select individual components instead of buying a pre-packaged unit.

Method of use 600 may comprise the following steps of assembling and using modular sanitation tray 100 according to user-preference including: step one 601 inserting at least one first dowel 225 into at least one first aperture 220 of at least one corner receiver 210; step two 602 attaching at least one corner receiver 210 to another corner receiver 210 via at least one first dowel 225; and optional step three 603 sliding a rack 250 into groove 240 of corner receiver 210 to make first tray 200 of modular sanitation tray system 100.

Modular sanitizing tray system components may be assembled in horizontal relation to each other by optional step four 604 inserting at least one first dowel 225 into at least one first aperture 220 of at least one side receiver 410; optional step five 605 attaching at least one side receiver 410 to corner receiver 210 and/or another side receiver 410; optional step 607 of attaching side receiver 410 to another side receiver 410 via at least one second aperture 415 and via at least one second dowel 419 and at least one second aperture 415; optional step six 608 sliding a rack 250 into groove 240 of corner receiver 210 or side receiver groove 430 of side receiver 410 to make a poly-sided modular sanitation tray 100.

Once modular sanitation tray system 100 is assembled in the user desired configuration, modular sanitation tray system 100 may optionally be assembled in a vertical configuration by optional step seven 609 placing first tray 200 on top of another first tray 200 via male coupler 230 and/or female coupler 235; and/or optional step 610 of placing second tray 400 on top of another second tray 400 via male coupler 230 and/or female coupler 235; and/or optionally placing first tray 200 on top of second tray 400 via male coupler 230 and/or female coupler 235. The user may repeat steps 601 through 609 as needed to create modular sanitation tray system 100 according to his or her specifications. Finally, step 610 inserting items into modular sanitation tray system 100 to be sanitized; and optionally step 611 disassembling modular sanitation tray system 100 for storage and/or transport.

It should be noted that the steps described in the method of use can be carried out in many different orders according to user preference. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations, and rearrangements can be readily envisioned to achieve substantially equivalent results, all of which are intended to be embraced within the spirit and scope of the invention.

What is claimed is:

1. A modular, assemblable sanitation tray system comprising:
   a plurality of dowels;
   a rack comprising a framework;
   a corner receiver; and
   a side receiver;
   wherein said corner receiver further comprises a groove, a male coupler, a female coupler, and a plurality of apertures;
   wherein said side receiver further comprises a groove, a male coupler, a female coupler, and a plurality of apertures; and
   wherein said plurality of apertures of each of the corner receiver and the side receiver form a plurality of cavities for removably receiving one of said plurality of dowels in each one of the cavities,
   wherein the groove of each of the corner receiver and the side receiver is configured for supporting the rack,
   wherein the male coupler and the female coupler of the corner receiver have complementary dimensions such that the male and female couplers are configured to engage female or male couplers, respectively, of another corner receiver, to enable vertical stacking with the another corner receiver, and
   wherein the male coupler and the female coupler of the side receiver have complementary dimensions such that the male and female couplers are configured to engage female or male couplers, respectively, of another side receiver, to enable vertical stacking with the another side receiver.

2. The modular, assemblable sanitation tray system of claim 1 wherein said groove of each of the side receiver and the corner receiver removably receives said rack.

3. The modular, assemblable sanitation tray system of claim 1 wherein said corner receiver is removably attached horizontally to another corner receiver via said plurality of dowels removably received by said plurality of apertures to form a tray.

4. The modular, assemblable sanitation tray system of claim 3 wherein said tray is capable of being stacked vertically and horizontally.

5. The modular, assemblable sanitation tray system of claim 1 wherein said corner receiver is removably attached horizontally to said side receiver via said plurality of dowels removably received by said plurality of apertures to form a tray.

6. The modular, assemblable sanitation tray system of claim 5 wherein said tray is capable of being stacked vertically and horizontally.

7. The modular, assemblable sanitation tray system of claim 1 wherein said side receiver is removably attached horizontally to another side receiver via said plurality of dowels removably received by said plurality of apertures to form a tray.

8. The modular, assemblable sanitation tray system of claim 7 wherein said tray is capable of being stacked vertically and horizontally.

9. The modular, assemblable sanitation tray system of claim 1, further comprising the another corner receiver, wherein said corner receiver is removably attached vertically to the male coupler or the female coupler of the another corner receiver via said female coupler or said male coupler, respectively.

10. The modular, assemblable sanitation tray system of claim 1, further comprising the another side receiver, wherein said side receiver is removably attached vertically to the male coupler or the female coupler of the another side receiver via said female coupler or said male coupler, respectively.

11. The modular, assemblable sanitation tray system of claim 1 further comprising at least one handle.

12. The modular assemblable sanitation tray system of claim 1 further comprising at least one instrument holder.

13. A kit comprising the modular, assemblable sanitation tray assembly of claim 1, wherein the kit includes a plurality of corner receivers including the corner receiver, a plurality of side receivers including the side receiver; the plurality of dowels, the rack, a handle, and an instrument holder.

14. A modular assemblable sanitation tray system comprising:
   a plurality of dowels;
   a rack comprising a framework;
   a corner receiver;
   a side receiver; and
   at least one instrument holder,
   wherein said corner receiver further comprises a groove, a male coupler, a female coupler, and a plurality of apertures;
   wherein said side receiver further comprises a groove, a male coupler, a female coupler, and a plurality of apertures; and wherein said plurality of apertures of each of the corner receiver and the side receiver form a plurality of cavities for removably receiving one of said plurality of dowels in each one of the cavities, wherein the groove of each of the corner receiver and the side receiver is configured for supporting the rack, wherein said at least one instrument holder secures surgical instruments within the modular sanitation tray system.

15. A sanitation tray system comprising:
a plurality of corner receivers;
a plurality of side receivers;
a rack; and
a plurality of dowels;
wherein each said corner receiver further comprises a male coupling element, a female coupling element, a plurality of apertures and a groove;
wherein each said side receiver further comprises a male coupling element, a female coupling element, a plurality of apertures and a groove;
wherein each of said plurality of dowels is configured to be inserted into one of said plurality of apertures of each said side receiver;
wherein each of said plurality of dowels is configured to be inserted into one of said plurality of apertures of each said corner receiver
wherein said rack fits into said groove of each of said side receivers;
wherein said rack fits into said groove of each of said corner receivers;
wherein the system is configured such that said rack, said plurality of dowels, and said plurality of corner receivers can be assembled to form a first rectangular tray;
wherein the system is further configured such that said rack, said plurality of dowels, said plurality of side receivers, and said plurality of corner receivers can be assembled to form a second rectangular tray having a different shape from the first rectangular tray;
wherein said male coupler of side receiver is configured to join with another female coupler of another side receiver for vertical stacking; and
wherein said male coupler of corner receiver is configured to join with another female coupler of another corner receiver for vertical stacking.

16. A rectangular sanitation tray having four corners and four sides, comprising:
four corner receivers forming the four corners of the tray, each of the corner receivers having a top side and a bottom side, and each of the corner receivers having a male coupler positioned on one of the top and bottom sides and a female coupler positioned on the other of the top and bottom sides;
a plurality of side receivers, including at least a first side receiver positioned along a first side of the four sides of the tray and a second side receiver positioned along a second side of the four sides of the tray opposite the first side, each of the side receivers having a top side and a bottom side, and each of the side receivers having a male coupler positioned on one of the top and bottom sides and a female coupler positioned on the other of the top and bottom sides;
a rack supported by the corner receivers and the side receivers to form a supporting surface of the tray, configured to support an instrument; and
a plurality of dowels connected to the corner receivers and the side receivers and extending between the corner receivers and the side receivers to further define the four sides of the tray,
wherein the tray is configured for vertical stacking with another identical tray, wherein the male coupler and the female coupler of each corner receiver have complementary dimensions such that the male and female couplers of each corner receiver are configured to engage female or male couplers, respectively, of another corner receiver of the another identical tray, to enable vertical stacking with the another corner receiver, and
wherein the male coupler and the female coupler of each side receiver have complementary dimensions such that the male and female couplers of each side receiver are configured to engage female or male couplers, respectively, of another side receiver of the another identical tray, to enable vertical stacking with the another side receiver.

17. The sanitation tray of claim 16, wherein each of the corner receivers and the side receivers has a groove that receives a portion of the rack therein to support the rack.

18. A rectangular sanitation tray having four corners and four sides, comprising:
four corner receivers forming the four corners of the tray, each of the corner receivers having a top side and a bottom side, and each of the corner receivers having a male coupler positioned on one of the top and bottom sides and a female coupler positioned on the other of the top and bottom sides;
a rack supported by the corner receivers to form a supporting surface of the tray, configured to support an instrument; and
a plurality of dowels connected to the corner receivers and extending between the corner receivers to define the four sides of the tray,
wherein the tray is configured for vertical stacking with another identical tray, wherein the male coupler and the female coupler of each corner receiver have complementary dimensions such that the male and female couplers of each corner receiver are configured to engage female or male couplers, respectively, of another corner receiver of the another identical tray, to enable vertical stacking with the another corner receiver.

19. The sanitation tray of claim 18, wherein each of the corner receivers has a groove that receives a portion of the rack therein to support the rack.

* * * * *